United States Patent
Taleb

(10) Patent No.: US 10,478,339 B2
(45) Date of Patent: Nov. 19, 2019

(54) SYSTEM AND METHOD FOR MANAGING PATIENT DATA DURING OPHTHALMIC SURGERY

(71) Applicant: Novartis AG, Basel (CH)

(72) Inventor: Michel Taleb, Berlin (DE)

(73) Assignee: Novartis AG (CH)

( * ) Notice: Subject to any disclaimer, the term of this patent is extended or adjusted under 35 U.S.C. 154(b) by 43 days.

(21) Appl. No.: 15/742,464

(22) PCT Filed: Jan. 19, 2017

(86) PCT No.: PCT/IB2017/050271
§ 371 (c)(1),
(2) Date: Jan. 5, 2018

(87) PCT Pub. No.: WO2018/134642
PCT Pub. Date: Jul. 26, 2018

(65) Prior Publication Data
US 2019/0000671 A1    Jan. 3, 2019

(51) Int. Cl.
*A61F 9/007* (2006.01)
*A61F 9/008* (2006.01)
(Continued)

(52) U.S. Cl.
CPC .......... *A61F 9/00745* (2013.01); *A61B 90/20* (2016.02); *A61B 90/98* (2016.02); *A61F 9/008* (2013.01); *A61F 9/00736* (2013.01); *A61F 9/00825* (2013.01); *G06K 7/10227* (2013.01); *G06K 7/10237* (2013.01); *G06K 7/10326* (2013.01); *G06K 7/10475* (2013.01); *A61F 2009/0087* (2013.01);
(Continued)

(58) Field of Classification Search
CPC ............ G06K 7/0008; G06K 7/10009; G06K 19/0723; G06K 7/10297; G06K 7/10366; G06K 19/0717; G06K 7/10128; G06K 19/07749
USPC ......................................................... 340/10.4
See application file for complete search history.

(56) References Cited

U.S. PATENT DOCUMENTS 5,658,303 A * 8/1997 Koepnick ............... A61F 9/013
                                                        128/899
6,117,126 A * 9/2000 Appelbaum ........... A61B 17/00
                                                        606/1
(Continued)

FOREIGN PATENT DOCUMENTS

WO    2016042705 A1    3/2016
WO    WO-2016042705 A1 * 3/2016 ........... A61B 90/361

*Primary Examiner* — Mark S Blouin
(74) *Attorney, Agent, or Firm* — Keiko Ichiye, Esq.

(57) ABSTRACT

The present disclosure provides a system and method for managing patient data during ophthalmic surgery. The systems and methods include an ophthalmic surgical device operable to receive data from a RFID chip. Data from the RFID chip is transmitted to a RFID read-write module operably coupled to the ophthalmic surgical system. A processor identifies the RFID chip based on the received data and determines whether the data stored to the RFID chip varies from data received from a surgical microscope by more than a predetermined percentage. The processor can generate a warning when the data stored to the RFID chip varies from data received from a surgical microscope by more than a predetermined percentage.

19 Claims, 4 Drawing Sheets

(51) Int. Cl.
- *G06K 7/10* (2006.01)
- *A61B 90/98* (2016.01)
- *A61B 90/20* (2016.01)
- *G02B 21/00* (2006.01)

(52) U.S. Cl.
CPC ............... *A61F 2009/00878* (2013.01); *A61F 2009/00887* (2013.01); *G02B 21/0012* (2013.01)

(56) References Cited

U.S. PATENT DOCUMENTS

| | | | | |
|---|---|---|---|---|
| 6,251,113 B1* | 6/2001 | Appelbaum | ........... | A61B 17/00 604/22 |
| 2006/0129140 A1* | 6/2006 | Todd | ................... | G06Q 10/087 606/1 |
| 2007/0027459 A1* | 2/2007 | Horvath | ................ | A61B 90/98 606/147 |
| 2013/0090634 A1* | 4/2013 | Loden | .................... | A61F 9/008 606/4 |

* cited by examiner

SYSTEM AND METHOD FOR MANAGING PATIENT DATA DURING OPHTHALMIC SURGERY

TECHNICAL FIELD

The present disclosure relates to ophthalmic surgery and surgical equipment, and more specifically, to the use of ophthalmic electronic identifiers on a wearable object. The electronic identifier can be used to transmit and receive data related to the patient's medical information and surgery plan.

BACKGROUND

Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is surgery performed on the eye or any part of the eye. Ophthalmic surgery is regularly performed to repair retinal defects, repair eye muscles, remove cataracts or cancer, or to restore or improve vision. Cataracts are the most common cause of vision loss in adults and can cause blindness in serious cases. Cataracts form due to age or disease can cause the lens to become less transparent, resulting in vision deterioration due to the diminished light that can be transmitted to the retina. Certain surgical procedures have been developed to treat cataracts and improve vision. An accepted treatment for cataracts is the surgical removal of the lens and replacement of the lens function by an artificial intraocular lens (IOL).

In cataract surgery the natural lens of the eye in which a cataract has developed is removed. The natural lens is replaced by an artificial lens. This surgical procedure is performed by a surgeon using a surgical microscope for observation. In some cases, the microscope may be connected to advanced imaging tools. The surgeon enters through the sclera or cornea, making an incision in the capsule sac within the inner margin of the iris. An ultrasonic probe is used to fragment/dissolve the natural lens. Then, the resulting solution is removed by suction using an aspirator, which may be part of the ultrasonic probe or a separate tool. After the natural lens has been removed, an artificial lens is inserted into the eye.

Ophthalmic procedures, including cataract surgery, require extreme precision due to the fragile nature of the eye. Certain ophthalmic surgical systems have been developed to improve precision and minimize potential damage from surgery. One example system is Alcon's VERION™ Image Guided System (Novartis AG, Switzerland). The VERION™ Image Guided System uses a number of measurements to increase precision in cataract surgery. These measurements include dynamic keratometry, limbus position and diameter, white-to-white horizontal distance, pupillometry, corneal reflex position, and eccentricity of the visual axis. Improved methods of storing and retrieving these types of measurements, and therefore improving the accuracy and safety of ophthalmic procedures, are desirable.

SUMMARY

According to one embodiment of the present invention, an ophthalmic surgical device includes a surgical microscope; a user interface; an RFID read-write module operable read an RFID chip and write patient data to an RFID chip associated with a patient; surgical instrumentation; warning system; and a processor operable to: receive data from the RFID chip associated with a patient; receive data from the surgical microscope associated with the patient; compare the data from the RFID chip to the data from the surgical microscope; determine whether the data from the RFID chip varies from the data from the surgical microscope by more than a predetermined percentage; generate a warning, if the data from the RFID chip and the data from the surgical microscope vary by more than the predetermined percentage; and transmit the warning to the warning system, causing the warning system to present a warning.

In a further embodiment, the ophthalmic surgical device of further includes an RFID chip associated with the ophthalmic surgical system.

In yet another embodiment, the ophthalmic surgical device further includes a control device associated with the ophthalmic surgical system, wherein the RFID chip is connected to the ophthalmic surgical device, the RFID chip operable to transmit data to the processor, and wherein the processor is further configured to generate and transmit a control signal to a control device, the control signal operable to pause the surgical instrumentation, when a warning is generated.

In another embodiment, the ophthalmic surgical device further includes a control device associated with the ophthalmic surgical system, wherein the RFID chip is connected to the ophthalmic surgical device, the RFID chip operable to transmit data to the processor, and wherein the processor is further configured to generate and transmit a control signal to a control device, the control signal operable to render the ophthalmic surgical system inoperable of continuing a surgical operation, when a warning is generated.

In yet another embodiment, the ophthalmic surgical device includes a processor, wherein the processor is further configured to require receipt of a manual confirmation input before permitting a user to continue a surgical operation when a warning is generated.

In another embodiment, the ophthalmic surgical device includes a processor, wherein the processor is further configured to require receipt of a manual confirmation input before permitting a user to continue a surgical operation when a warning is generated.

In still another embodiment, the ophthalmic surgical device includes a device for manual confirmation of an adjustment, wherein the device for manual confirmation of an adjustment is selected from at least one of: a button, a switch, a key, and a joystick.

In a different embodiment, the ophthalmic surgical device includes a device for manual confirmation of an adjustment, wherein the device for manual confirmation of an adjustment is selected from at least one of: a button, a switch, a key, and a joystick.

In another embodiment, the ophthalmic surgical device includes a warning system, wherein the warning system comprises a display operable to present a pictorial representation, and wherein the processor is further configured to generate the pictorial representation to indicate the warning generated, when a warning is generated.

In yet another embodiment the ophthalmic surgical device includes a warning system, wherein the warning system comprises at least one of: a speaker, a light indicator, and a haptic feedback device, to indicate that a warning was generated.

In still another embodiment, the ophthalmic surgical device receives data from the RFID chip, wherein the data from the RFID chip includes a first image of an eye of the patient.

In another embodiment, the ophthalmic surgical device receives data from the surgical microscope, wherein the data from the surgical microscope includes a second image of the eye of the patient, the second image being acquired using the surgical microscope, and wherein the processor operable to compare the data from the RFID chip to the data from the surgical microscope further comprises the processor operable to compare the first image to the second image.

The above systems may be used with the above methods and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

Ophthalmic procedures, including cataract surgery, require extreme precision due to the fragile nature of the eye. Certain ophthalmic surgical systems have been developed to improve precision and minimize potential damage from surgery. In ophthalmic surgery, a surgeon may need to verify that the patient's eye has not changed significantly since a pre-operative visit. The accurate storage of important measurements and images of the eye is important in order to ensure the best possible vision for the patients in need of cataract surgery. Oftentimes, it is useful to store important patient data in multiple places to decrease the likelihood of error. One way to decrease the possibility of error with respect to pre-operative patient data is the use of an electronic identifier associated with a particular patient.

One way to store important patient data is to utilize a Radio Frequency Identification system (RFID). RFID systems use electronic chips or transponders to store data. These systems use electromagnetic fields to automatically identify and track chips. Some RFID systems use passive chips that are activated when they are physically within a certain proximity of radio transmitted signal. Other RFID systems use active chips that include an independent power source to operate independently.

Figure 1A:
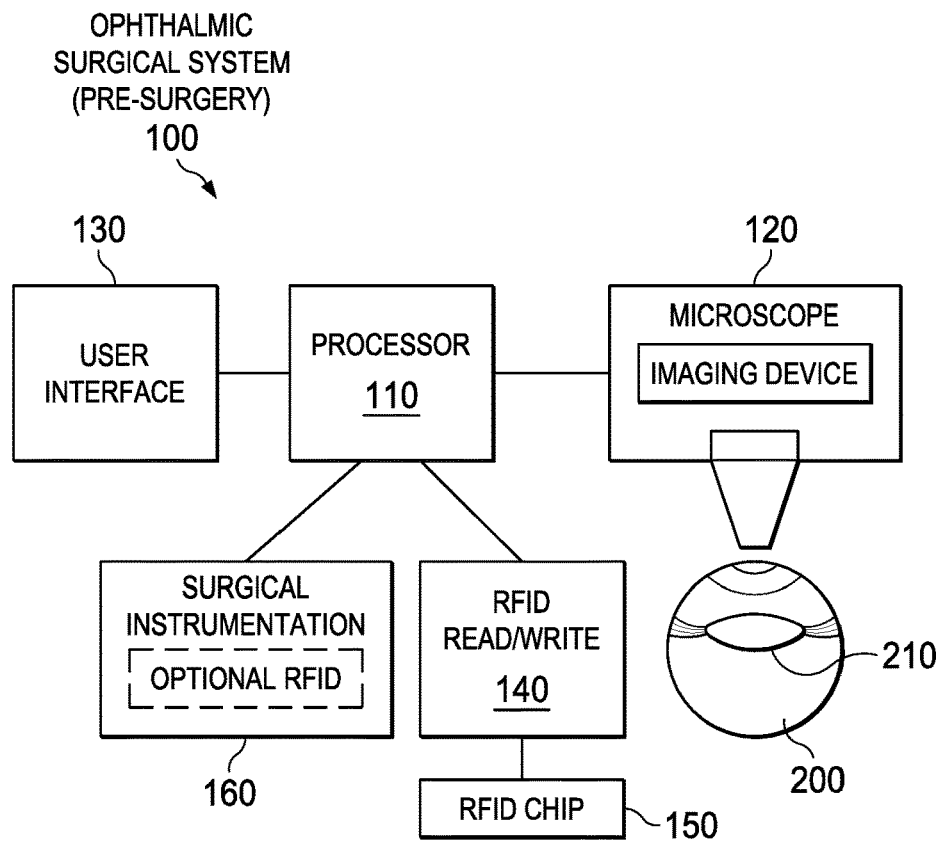
FIG. 1A is a schematic representation of an ophthalmic surgical system prior to execution of an ophthalmic surgery procedure.

Referring now to the figures, FIG. 1A is a schematic representation of an ophthalmic surgical system 100 prior to execution of an ophthalmic surgery procedure.

As shown, the ophthalmic surgical system 100 includes a processor 110, a surgical microscope 120, a user interface 130, an RFID read-write module 140, an optional RFID chip 150, and surgical instrumentation 160.

Processor 110 may include, for example a microprocessor, microcontroller, digital signal processor (DSP), application specific integrated circuit (ASIC), or any other digital or analog circuitry configured to interpret and/or execute program instructions and/or process data. In some embodiments, processor 110 may interpret and/or execute program instructions and/or process data stored in a memory. The memory may be configured in part or whole as application memory, system memory, or both. The memory may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

The ophthalmic surgical system 100 also includes a user interface 130 and a surgical microscope 120 for observing an eye during surgery. Surgical microscope 120 may any tool suitable for visually inspecting the eye and may include electronic and/or optical views. For example, surgical microscope 120 may be a light or electron microscope. Surgical microscope 120 may be a standalone microscope or may be integrated into ophthalmic surgical system 100, for example, such that enlarging and focusing components of the surgical microscope are integrated into system 100.

The user interface 130 may include any suitable output device for generating an alignment guide for the eye. User interface 130 may include a printer, a video display, an image display, or a light projector. In some embodiments, the user interface 130 may be coupled to the surgical microscope 120 so that the image is projected into the view of the surgical microscope 120. The user interface 130 may further include any kind of keyboard, switch, knob, pedal, button, pointing device, or other suitable component for receiving selections of surgical parameters from the user.

In addition, ophthalmic surgical system 100 includes an RFID read-write module 140. The RFID read-write module 140 is an exemplary RFID system that can be used with embodiments of this invention. The RFID read-write module 140 interacts with an RFID chip 150. The RFID chip 150 typically includes an Integrated Circuit (IC), such as an Application Specific Integrated Circuit (ASIC), that includes a memory for storing data. A transponder is activated by Radio Frequency (RF) instruction or signal from the reader, which is sent through the reader antenna, for example, in response to a micro-controller unit, and received by an antenna of the transponder to wirelessly write data to or read data from the memory of the transponder. RFID chip 150 may be considered part of the ophthalmic surgical system 100 when interacting with ophthalmic surgical system 100, but ophthalmic surgical system 100 may interact with multiple different RFID chips 150 over time and is typically provided without an RFID chip 150.

For example, when the RFID chip 150 is to be read, the RFID reader sends out a 134.2 KHz power pulse to the antenna lasting approximately 50 ms. The magnetic field generated is collected by the antenna in the RFID chip 150 that is tuned to the same frequency. This received AC energy is rectified and stored in a small capacitor within the transponder. After completion of the power pulse, the transponder transmits back its data, using the energy stored in the capacitor as a power source. In this exemplary implementation, a total of 128 bits are transmitted (including error detection information) over a period of 20 ms. This data is received by the antenna and decoded by the reader unit and controller. The capacitor is discharged after the data has been transmitted, and the transponder is reset and ready for the next read cycle.

The RFID configuration described above is "passive" because the transponder is powered by power stored in a capacitor that is generated by the RF signal from the reader. Thus, a passive RFID identifier is normally inactive and does not have an independent power source. The RFID chip 150 may also be active if a separate power source or battery is provided. Further details concerning the manner in which RFID systems operate is well known in the art and, therefore, is not discussed in further detail in this specification. For purposes of explanation, not limitation, this specification refers to RFID components that are used for transmitting data between an ophthalmic surgical system 100 and an RFID chip 150. However, persons skilled in the art will recognize that other transmitter, receiver and transceiver components can also be utilized.

When RFID components are applied to embodiments to provide communications between a ophthalmic surgical system 100 and an RFID chip 150, the RFID chip 150 can be physically included with or attached to an armband. In another embodiment, the RFID chip 150 may be physically included with or attached to another wearable object that the patient may keep possession of between doctor visits. The RFID chip 150 includes the identification and, if applicable, other data relating to the component. In one embodiment, the RFID chip includes information on plurality of parameters about the patient eye 220. The processor 110 includes software and/or hardware to implement the criteria to determine whether data sent by the RFID chip 150 of the patient and received by the RFID read-write module 140 of the ophthalmic surgical system 100 indicates that the surgery should proceed. The ophthalmic surgical system 100 can operate with multiple RFID chips 150 that correspond to different patients, the same patient at different times, or in connection with different ophthalmic surgery procedures. Data stored to the RFID chip 150 may be encrypted to prevent unauthorized access.

The ophthalmic surgical system 100 further includes surgical instrumentation 160. Surgical instrumentation 160 may include surgical lasers, cutting instruments, blunt instruments, suction instruments, and imaging instruments. Surgical instrumentation 160 may further include any type of component or machine used in ophthalmic surgery, including but not limited to handpieces, pneumatic systems, laser sources, illumination sources. Such components may be used in ophthalmic techniques such as phacoemulsification, or any of the other various ophthalmic surgical methods known to one of skill in the art. Surgical instrumentation 160 may be integrated into the ophthalmic surgical system 100. In other embodiments, surgical instrumentation 160 may be separate from the ophthalmic surgical system 160 and operable to interface with ophthalmic surgical system 100.

Ophthalmic surgical system 100 also includes pre-operation patient eye 200. The pre-operation patient eye 200 includes a lens 210. Cataracts form due to age or disease can cause the lens 210 to become less transparent, resulting in vision deterioration due to the diminished light that can be transmitted to the retina.

Figure 1B:
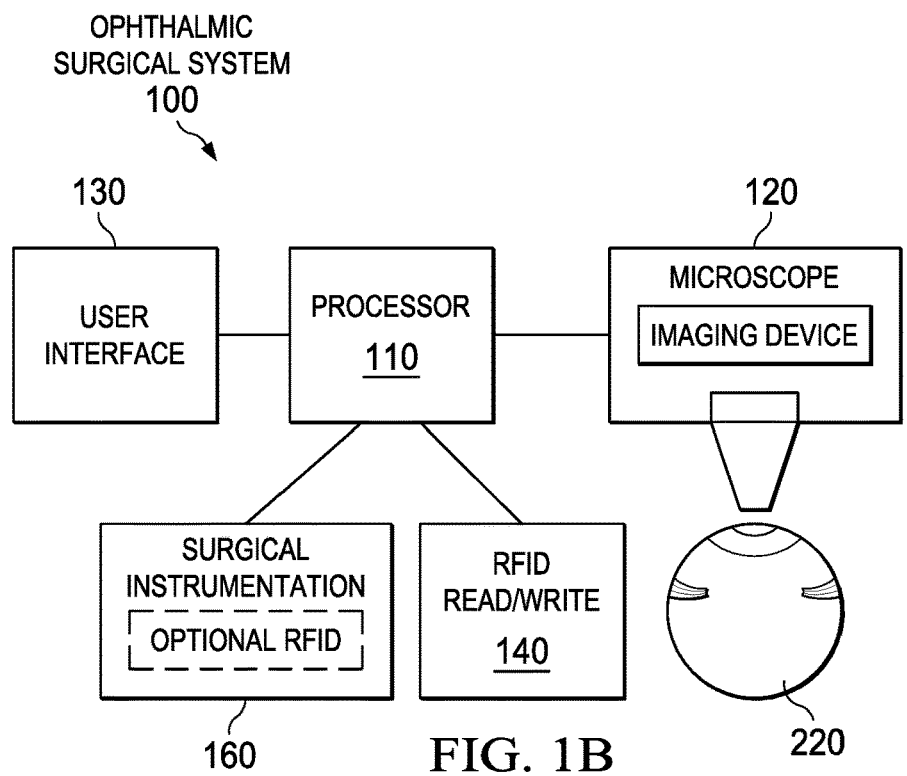
FIG. 1B is a schematic representation of an ophthalmic surgical system during execution of an ophthalmic surgery procedure.

FIG. 1B is a system is a schematic representation of an ophthalmic surgical system 100 during execution of an ophthalmic surgery procedure. During the surgery, there is a period of time where the patient eye 220 is aphakic. An aphakic eye does not have a lens.

Figure 1C:
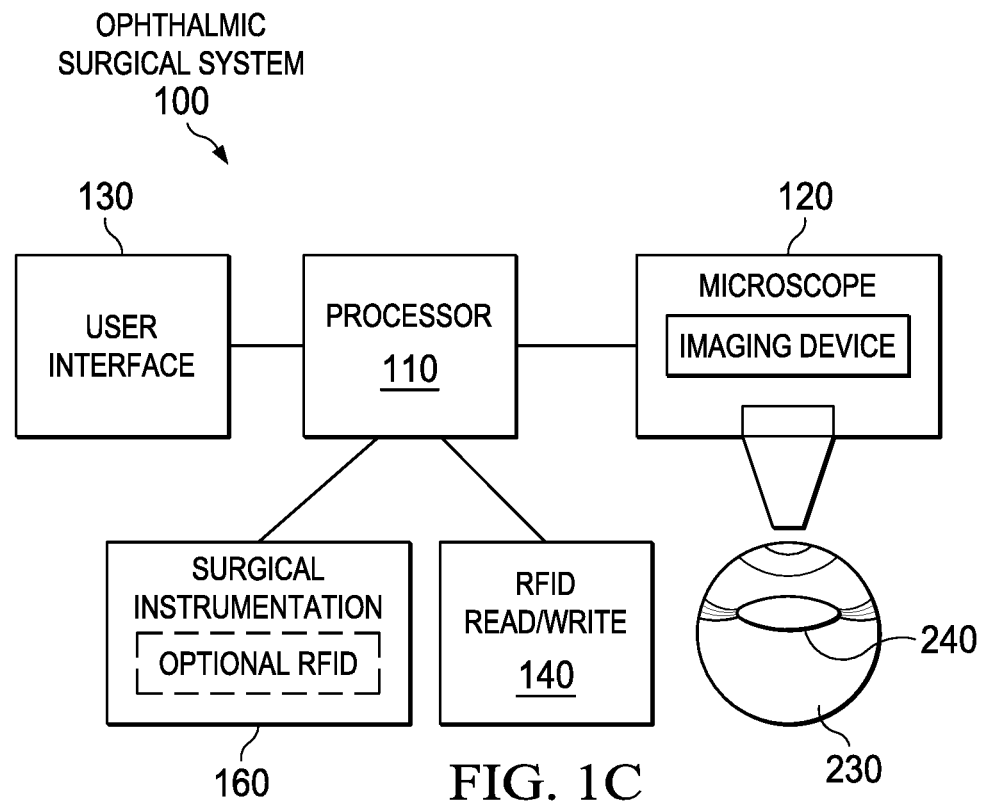
FIG. 1C is a schematic representation of an ophthalmic surgical system after execution of an ophthalmic surgery procedure.

FIG. 1C is a system is a schematic representation of an ophthalmic surgical system 100 after execution of an ophthalmic surgery procedure. The post-operative patient eye 230 includes an artificial intraocular lens (IOL) 240.

Figure 2:
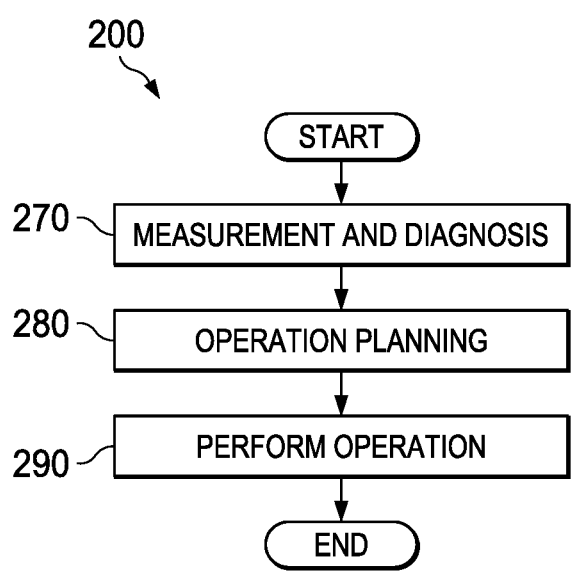
FIG. 2 is a flowchart of a method for using an ophthalmic electronic identifier on a wearable object, wherein the electronic identifier can be used to transmit and receive data related to the patient's medical information and surgical plan.

FIG. 2 is a flowchart of a method for using an ophthalmic electronic identifier on a wearable object, wherein the electronic identifier can be used to transmit and receive data related to the patient's medical information and surgical plan. At step 270, the ophthalmic surgical system commences by taking a number of measurements of the patients pre-operative eye 210. These measurements may include dynamic keratometry, limbus position and diameter, white-to-white horizontal distance, pupillometry, corneal reflex position, and eccentricity of the visual axis. The ophthalmic surgical system may also take images of the pre-operative patient eye 210. This data is used to make a diagnosis. In one example, the data indicates that the patient requires cataract surgery. The patient data, including measurements and images, is written to the RFID chip 150 using RFID read-write module 140.

At step 280, the surgeon uses an ophthalmic surgical system 100 to develop a surgical plan for the patient based on the patient data collected at step 270.

Finally, at step 290 the surgeon executes a surgical plan using the ophthalmic surgical system 100.

Figure 3A:
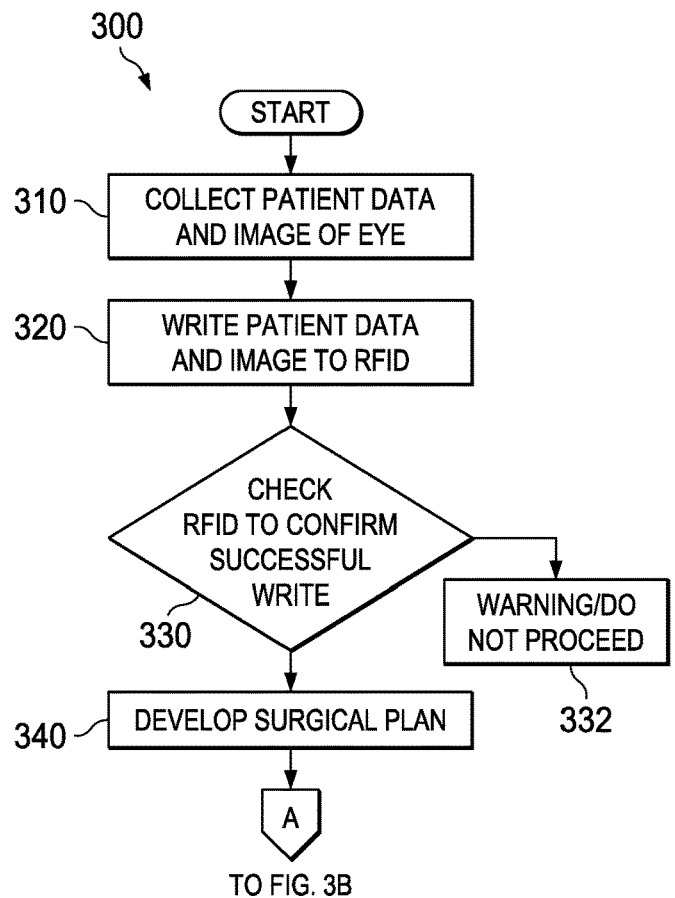
FIG. 3A is a flowchart of a method for collecting and storing patient information on an electronic identifier prior to an ophthalmic surgery procedure.

FIG. 3A is a flowchart showing additional details about the measurement and diagnosis step 270 and the operation planning step of FIG. 2. At step 310, data may be received by the ophthalmic surgical system 100 relating to a plurality of measurements about the pre-operative patient eye 200 and the pre-operation patient lens 210 using imaging device 120. Data measurements may include dynamic keratometry, limbus position and diameter, white-to-white horizontal distance, pupillometry, corneal reflex position, and eccentricity of the visual axis. Further, at least one image of the pre-operation patient eye 200 and the pre-operation patient lens 210 may be collected with imaging device 120.

At step 320, data received from the pre-operative scan is written to the RFID chip 150 by the RFID read-write module 140.

At optional step 330, the ophthalmic surgical system 100 checks the RFID chip 150 to confirm that the data has been correctly written by the RFID read-write module 140. At this step, the ophthalmic surgical system 100 may also check to see that the data is consistent with the patient data otherwise associated with the patient eye 200. This data may include historical patient data. If the data read by RFID read-write module 140 from the RFID chip 150 is not consistent with patient data otherwise associated with the patient, the system may proceed to step 332 and produce a warning. If the data read by the RFID read-write module 140 from the RFID chip 150 is consistent with patient data otherwise associated with the patient, the system may continue to step 340 and develop a surgical plan.

Figure 3B:
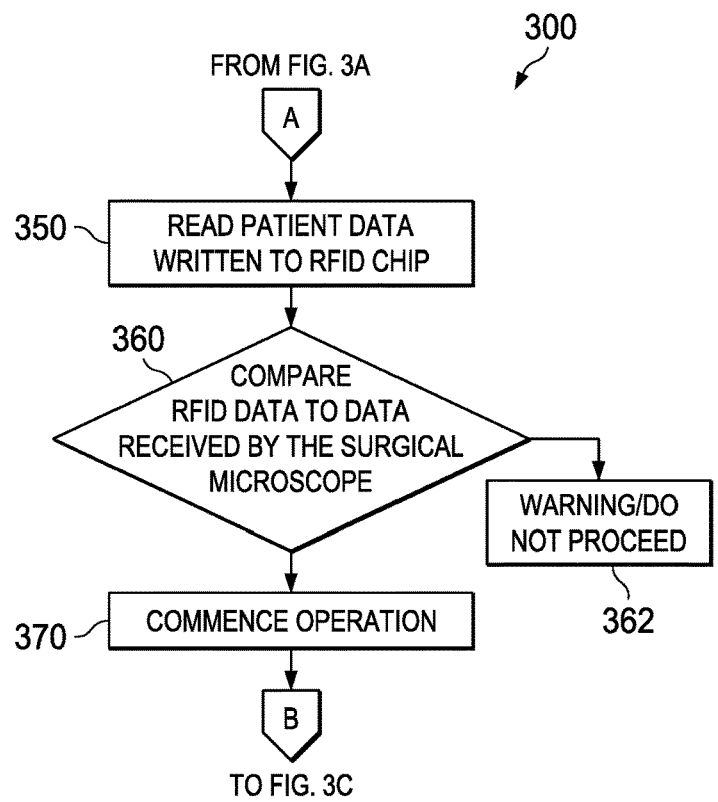
FIG. 3B is a flowchart of a method for using an electronic identifier in connection with an ophthalmic surgery procedure.

FIG. 3B is a flowchart showing additional details about the perform operation step 290 of FIG. 2. At step 350, the patient is registered with the ophthalmic surgical system 100 in preparation for the planned procedure. Data stored to the RFID 150 about the pre-operative patient eye 200 and the pre-operative patient lens 210 is read by RFID read-write module 140. Next, at step 360, the ophthalmic surgical system 100 compares the data stored to the RFID 150 to data received by the ophthalmic surgical system using surgical microscope 120 or other methods of collecting patient data. In one embodiment, the ophthalmic surgical system 100 compares the image of the patient eye 200 stored to the RFID chip 150 and an image of the patient eye received by the surgical microscope 120. In another embodiment, the surgical system 100 compares at least one parameter stored to the RFID chip 150 to at least one parameter measured by the ophthalmic surgical system. The parameters stored in the RFID chip correspond to patient data. In another embodiment, the ophthalmic surgical system 100 compares a plurality of parameters stored to the RFID chip 150 to a plurality of parameters measured by the ophthalmic surgical system. In yet another embodiment, the ophthalmic surgical system 100 compares all parameters stored to the RFID chip 150 to all parameters measured by ophthalmic surgical system.

If the data stored to RFID 150 differs in a measured parameter by more than a predetermined percentage from that received by the ophthalmic surgical system 100, the system proceeds to step 362 and produces a warning or fails to initiate the procedure. Comparison step 360 helps to ensure that the surgical plan can be altered in the case that a patient's eye has changed so drastically in the time period since the last scan. Further, this step ensures that surgery is performed on the correct patient eye 200 using the correct surgical plan generated in step 340.

The warning system may be integrated with the user interface 130. The warning system may include a display and the processor 110 may also generate a pictorial representation and transmit the pictorial representation, for example, to user interface 130. User interface 130 may include multiple displays and may be a screen, a heads-up display, or a combination. Alternatively, the warning system may be a separate component of the ophthalmic surgical system 100. The warning generated may be transmitted to a warning system that does not include a display, and without generating a pictorial representation that includes the warning when a warning is generated. The warning system may include a speaker, light indicator, haptic feedback device, or other device that indicates to the user that a warning was generated.

When a warning threshold has been met or exceeded, a control signal may be generated, the control signal to pause or turn off the ophthalmic surgical system 100. The system may be configured to automatically pause or turn off the ophthalmic surgical system 100 when a warning threshold is met. In the event the surgical system is automatically paused or turned off, a warning may indicate to the user that the surgical system has been paused or turned off. Similarly, the system may be configured to notify the user that manual confirmation is required to pause or turn off the surgical system. In one embodiment, the warning may be overridden and the operator can continue on to step 370 and perform the operation. In another embodiment, the warning may not be overridden and will prevent the operation from proceeding.

The ophthalmic surgical system 100 may not allow the warning to be overridden in a scenario, for example, where the comparison step 360 indicates that the patient prepared for surgery is not same patient with data written to RFID chip 150. As another example, the warning may not be overridden where more than one parameter exceed a predetermined variation.

Any warning described herein may be, for example, in the form of a colored light, a blinking light, a flashing light, a sound, an alarm, a whistle, a graphic, or any other signal that indicates to the user that that a warning was generated. The warning may be presented to the user in real time, preferably as soon as it is determined that a warning is required. Real time may mean in less than half a second, in less than one second, or otherwise in less than the normal reaction time of a user based on visual information.

If the data stored to RFID 150 does not differ in a measured parameter by more than a predetermined percentage from that received by the ophthalmic surgical system 100, the system proceeds to step 370. At step 370 the ophthalmic surgical procedure commences.

Figure 3C:
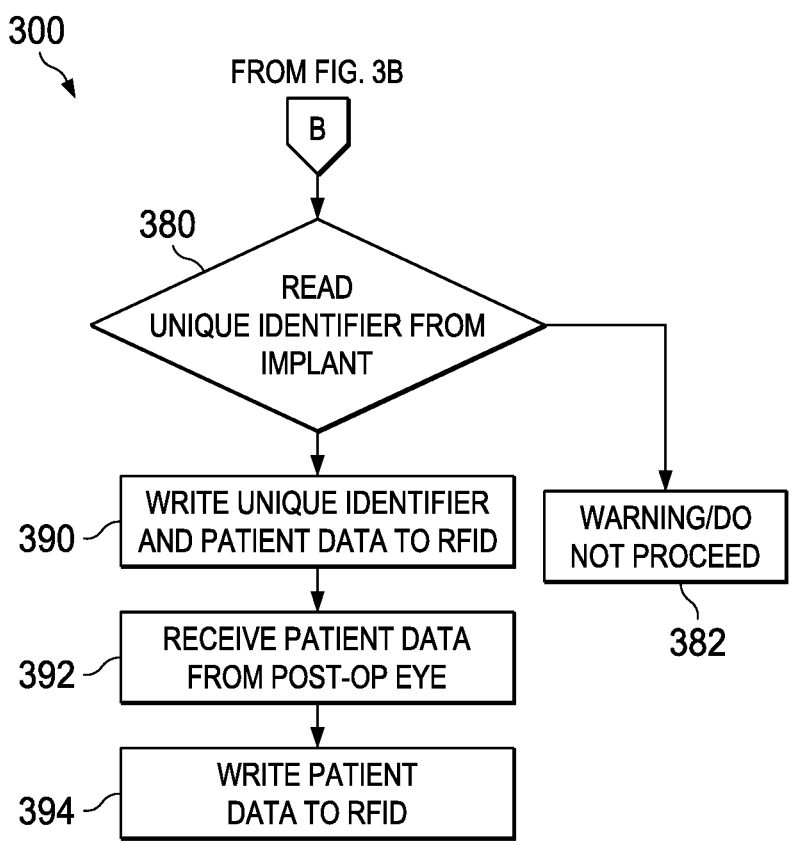
FIG. 3C is a flowchart showing additional details of a step of the flowchart of FIG. 2.

FIG. 3C is a flowchart showing additional details about the perform operation step 290 of FIG. 2. Steps shown in FIG. 3C are optional. During the procedure, the damaged patient lens 210 is removed using one or more of the surgical instrumentation 160. When the patient eye is without a lens, it is aphakic (220), as shown in FIG. 1B. In one embodiment, the RFID read-write module 140 may write data of the aphakic eye 220 to the RFID chip 150.

At step 380, the RFID read-write module 140 reads an RFID chip associated with the intraocular lens (IOL) 240 that has been selected for the patient. The ophthalmic surgical system 100 may check to confirm that the selected IOL is intended for the patient. If the IOL is not correct, the system proceeds to step 382 and produces a warning or fails to continue the procedure. If the IOL is correct, the system proceeds to step 390. At step 390, the RFID read-write module writes data pertaining to a scan of the aphakic patient eye 220 and the selected IOL 240 to the RFID chip 150.

The system then proceeds to step 392, in which the ophthalmic surgical system 100 performs a final scan of the patient's post-operative eye 230. In one embodiment, the procedure may continue to optional step 394. At step 394, the RFID read-write module 140 may write data associated with the post-surgical eye 230 to the RFID chip 150.

The above disclosed subject matter is to be considered illustrative, and not restrictive, and the appended claims are intended to cover all such modifications, enhancements, and other embodiments which fall within the true spirit and scope of the present disclosure.

Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. An ophthalmic surgical device comprising:
   a surgical microscope;
   a user interface;
   an RFID read-write module operable read an RFID chip and write patient data to an RFID chip associated with a patient;
   surgical instrumentation;
   a warning system; and a processor operable to:
　receive data from the RFID chip associated with a patient, the data from the RFID chip comprising a first measurement of an eye;
　receive data from the surgical microscope associated with the patient, the data from the surgical microscope comprising a second measurement of the eye;
　compare the data from the RFID chip to the data from the surgical microscope;
　determine whether the eye has changed by determining whether the data from the RFID chip varies from the data from the surgical microscope by more than a predetermined percentage;
　generate a warning, if the data from the RFID chip and the data from the surgical microscope vary by more than the predetermined percentage; and
　transmit the warning to the warning system, causing the warning system to present a warning.

2. The ophthalmic surgical device of claim 1, further comprising:
　an RFID chip associated with the ophthalmic surgical system.

3. The ophthalmic surgical device of claim 1, further comprising:
　a control device associated with the ophthalmic surgical system, wherein the RFID chip is connected to the ophthalmic surgical device, the RFID chip operable to transmit data to the processor, and wherein the processor is further configured to generate and transmit a control signal to a control device, the control signal operable to pause the surgical instrumentation, when a warning is generated.

4. The ophthalmic surgical device of claim 1, further comprising:
　a control device associated with the ophthalmic surgical system, wherein:
　the RFID chip is connected to the ophthalmic surgical device, the RFID chip operable to transmit data to the processor; and
　the processor is further configured to generate and transmit a control signal to a control device, the control signal operable to render the ophthalmic surgical system inoperable of continuing a surgical operation, when a warning is generated.

5. The ophthalmic surgical device of claim 3, wherein the processor is further configured to require receipt of a manual confirmation input before permitting a user to continue a surgical operation when a warning is generated.

6. The ophthalmic surgical device of claim 4, wherein the processor is further configured to require receipt of a manual confirmation input before permitting a user to continue a surgical operation when a warning is generated.

7. The ophthalmic surgical device of claim 3, wherein the device for manual confirmation of an adjustment is selected from at least one of: a button, a switch, a key, and a joystick.

8. The ophthalmic surgical device of claim 4, wherein the device for manual confirmation of an adjustment is selected from at least one of: a button, a switch, a key, and a joystick.

9. The ophthalmic surgical device of claim 1, wherein:
　the warning system comprises a display operable to present a pictorial representation; and
　the processor is further configured to generate the pictorial representation to indicate the warning generated, when a warning is generated.

10. The ophthalmic surgical device of claim 1, wherein the warning system comprises at least one of: a speaker, a light indicator, and a haptic feedback device, to indicate that a warning was generated.

11. The ophthalmic surgical device of claim 1, wherein the data from the RFID chip includes a first image of the eye of the patient.

12. The ophthalmic surgical device of claim 11, wherein:
　the data from the surgical microscope includes a second image of the eye of the patient, the second image being acquired using the surgical microscope; and
　the processor operable to compare the data from the RFID chip to the data from the surgical microscope further comprises the processor operable to compare the first image to the second image.

13. A method for performing ophthalmic surgery, comprising:
　receiving first data representing a patient eye from an RFID chip associated with the patient, the data from the RFID chip comprising a first measurement of the eye;
　receiving second data representing the patient eye from a surgical microscope, the data from the surgical microscope comprising a second measurement of the eye;
　comparing the first data and the second data;
　determining whether the eye has changed by determining whether the first data varies from the second data by more than a predetermined percentage;
　generating a warning, if the first data and the second data vary by more than the predetermined percentage; and
　transmitting the warning to a warning system, causing the warning system to present a warning.

14. The method of claim 13, further comprising:
　pausing the surgical instrumentation, when a warning is generated.

15. The method of claim 13, further comprising:
　rendering the ophthalmic surgical system inoperable of continuing a surgical operation, when a warning is generated.

16. The method of claim 14, further comprising:
　requiring receipt of a manual confirmation input before permitting a user to continue a surgical operation, when a warning is generated.

17. The method of claim 15, further comprising:
　requiring receipt of a manual confirmation input before permitting a user to continue a surgical operation, when a warning is generated.

18. The method of claim 13, wherein the first data includes a first image of the patient eye.

19. The method of claim 18, wherein the second data includes a second image of the patient eye, and wherein comparing the first data and the second data includes comparing the first image and the second image.

* * * * *